United States Patent [19]

Bartos

[11] 4,354,488

[45] Oct. 19, 1982

[54] NOSE MASK GAS DELIVERY DEVICE

[75] Inventor: Donald M. Bartos, Midland, Mich.

[73] Assignee: Dow Corning Corporation, Midland, Mich.

[21] Appl. No.: 209,784

[22] Filed: Nov. 24, 1980

[51] Int. Cl.³ .......................................... A61M 16/00
[52] U.S. Cl. ........................... 128/205.25; 128/207.13
[58] Field of Search ...................... 128/203.28, 205.25, 128/206.21, 206.28, 207.13, 910

[56] References Cited

U.S. PATENT DOCUMENTS

| | | | |
|---|---|---|---|
| 2,174,523 | 10/1939 | Manson | 128/206.28 |
| 2,241,535 | 5/1941 | Boothby et al. | 128/207.13 |
| 2,499,650 | 3/1950 | Kaslow | 128/204.18 |
| 2,764,152 | 9/1956 | Osterberg | 128/205.25 |
| 2,792,000 | 5/1957 | Richardson | 128/207.13 |
| 2,831,487 | 4/1958 | Tafilaw | 128/205.25 |
| 2,859,748 | 11/1958 | Hudson | 128/207.13 |
| 2,868,199 | 1/1959 | Hudson | 128/207.18 |
| 3,682,171 | 8/1972 | Dali et al. | 128/207.18 |
| 3,990,112 | 11/1976 | Ciffolillo | 128/910 |
| 4,216,769 | 8/1980 | Grimes | 128/207.13 |
| 4,231,363 | 11/1980 | Grimes | 128/205.25 |

FOREIGN PATENT DOCUMENTS 80647 6/1951 Czechoslovakia .
27599 of 1903 United Kingdom .

OTHER PUBLICATIONS

Nursing Photobook ™, Providing Respiratory Care, Robinson and Russo, Editors, Intermed. Communications, Inc. Horsham, PA 19044, pp. 104–107 (1979).

Primary Examiner—Henry J. Recla
Attorney, Agent, or Firm—Richard E. Rakoczy

[57] ABSTRACT

A nose mask for administering one or more gases such as oxygen to a human being comprises, in combination, (I) a shell having a front portion, a rear portion and a first opening comprising substantially the entire horizontal area beneath the wearer's nose and (II) a hollow gas delivery tube containing at least one gas delivering and dispersing means. The mask enables a wearer to breathe, eat and converse in a substantially normal fashion while efficiently providing the wearer with a cloud of gas (enriched in the gas or gases being delivered) directly beneath the nose and in front of the mouth of the wearer. The mask is particularly useful in long-term oxygen therapy applications.

17 Claims, 14 Drawing Figures

NOSE MASK GAS DELIVERY DEVICE

BACKGROUND OF THE INVENTION

This invention relates to a nose mask for administering one or more gases such as oxygen to a human being.

As of 1978, about three million Americans were diagonosed as having chronic obstructive pulmonary disease (COPD). The term "COPD" is generally applied to chronic respiratory disease processes characterized by the persistent obstruction of bronchial air flow. Typical COPD patients are those suffering from conditions such as bronchitis, cystic fibrosis, asthma or emphysema. The condition of a great number of COPD patients can be improved by supplying them with a source of pure oxygen gas or a mixture of oxygen and other inert gases such that the concentration of oxygen in the mixture is greater than that amount found in air (about 21 percent by volume). Depending upon the severity of their condition, COPD patients may require administration of additional oxygen (oxygen therapy) for a period of from a few hours a day up to twenty-four hours per day for a period of time which may extend for weeks to years. In view of the potential for long-term usage, the device employed to deliver oxygen to the patient should be comfortable, efficient, simple in design, disposable or easily cleaned and sterilized, economical in terms of oxygen usage and should permit the wearer to breathe, eat and converse in as normal a fashion as possible.

The same factors are applicable to an oxygen delivery device used in a hospital for any patient requiring the administration of additional oxygen. A simple, comfortable device which places a minimum amount of restrictions on the patient's freedom to breathe, eat and talk is more likely to be worn by the patient. These factors become especially important when the device is used by a patient in his own home since hospital-type supervision and assistance is generally not available either (a) to require such a patient to wear an uncomfortable mask for the amount of time required by his condition or (b) to assist him in the event that a malfunction occurs in a more complicated delivery device such as one having a rebreather bag attached.

Various approaches to provide a device for administering additional oxygen to a patient have been taken in the past. Face masks which cover the nose and mouth both effectively and economically administer oxygen, but have the disadvantages of being hot and confining, interfere with eating and speaking and are said to be impractical for long-term oxygen therapy.

Nasal cannulas such as those described in U.S. Pat. Nos. 2,499,650 (Kaslow—patented Mar. 7, 1950) and 2,868,199 (Hudson—patented Jan. 13, 1959) have been used to avoid the confinement inherent in face masks covering the mouth. The cannulas are simply a hollow tube running directly beneath the wearer's nose which contain openings or prongs which direct the gas directly into the wearer's nostrils. The cannula also has the advantages of being comfortable, inexpensive and a means for providing a continuous source of gas, but has the disadvantages of (a) tending to dry out the mucous membranes of the wearer's nose, especially when worn for an extended period of time, (b) not being useful when the patient has complete nasal obstruction, and (c) being easily dislodged so that the wearer should be alert and cooperative while the device is being worn to help keep the cannula in place. One means for alleviating the problem of dislodgement is described in U.S. Pat. No. 3,682,171 (Dali et al.—patented Aug. 8, 1972) wherein the cannula is kept in place by means of an arch-like nose bridge. The improvement described by Dali et al. minimizes one disadvantage of the nasal cannula, but does not minimize the other two.

Another delivery system employed is a nasal catheter which is a tube containing a number of gas delivery openings in one end which is inserted into the patient's nostril. While it possesses most of the advantages of the nasal cannula and is not dislodged as easily as the cannula, it is less comfortable than the nasal cannula, it can dry the nostrils and mucous membranes, it must be moved from one nostril to the other periodically and it may clog with secretions.

Another delivery system is the apparatus for delivering and permitting normal breathing of mixtures of gases taught in U.S. Pat. No. 2,241,535 (Boothby et al.—patented May 13, 1941). It is basically a mask covering the entire nose which is fed by two gas delivery tubes which encircle the wearer's mouth and lead to a rebreather bag, thereby permitting normal breathing of various concentrations of gases, particularly oxygen. The Boothby et al. apparatus is said to be capable of effectively and economically delivering up to 100 percent oxygen without having the wearer experience appreciable discomfort or irritation. It still possesses the disadvantage of having a bulky rebreather bag. The mask does not appear to be suitable for long-term usage due to its complexity and restrictions on movement caused by the tubes and bag hanging down in front of the wearer. Furthermore, the nose is entirely enclosed by the mask and thereby offers some resistance to normal breathing and can also result in moisture condensing on the bottom of the mask.

A simple, inexpensive nose mask which contains a single gas delivery tube having a single opening which positioned such that the entering gas stream does not directly flow against the face is taught in U.S. Pat. No. 2,859,748 (Hudson—patented Nov. 11, 1958). While it has many advantages, it still covers the entire nose thereby presenting some resistance to exhalation through the nose and could become uncomfortably warm and/or become wet as a result of water vapor (from the patient's breath or from water vapor added to the oxygen) condensing on the inside surface of the mask.

U.S. Pat. No. 2,174,523 (Manson—patented Oct. 3, 1939) teaches a face mask for airplane pilots which is said to permit normal unrestricted breathing and exhalation through the nose with ample provision for vocal communication. The nose is covered from the bridge to the lower edge by the mask. An oxygen distributor composed of two hollow tubes with a number of gas delivery openings is placed directly under the nose and in front of the mouth so that oxygen being supplied is directed at the nose and mouth of the wearer by a baffle plate to permit normal unrestricted breathing. Fogging of the pilot's goggles and formation of ice around the oxygen distribution tubes due to restricted exhalation is said to be avoided in this device because of the provision for unrestricted exhalation (around the sides). It does have the disadvantage of preventing one from eating since the mouth is covered. Furthermore, the mask covers a good portion of the wearer's face and would tend to be warm and uncomfortable over a long period of use.

Czechoslovakian Patent Specification No. 80,647 (Eng. Karel Urban—protected from Aug. 15, 1950) describes an air curtain which is basically a tube containing a downwardly-disposed single row of openings mounted on the edge of a holder resembling an eyeglass frame. The tube is held at about the level of the lower edge of the nose to provide an air curtain across the face to protect a worker such as a painter from vapors and airborne particles while providing him with a continuous supply of clean and fresh air. However, the configuration taught appears to require a large gas flow to be effective for its stated purpose which is an "air-curtain" barrier and does not appear to be designed for use in efficiently and economically administering gases to a human being.

A further summary of state of the art relating to oxygen delivery devices can be found on pages 104 to 107 of "Nursing Photobook TM, Providing Respiratory Care," Robinson and Russo, editors, Intermed Communications, Inc., Horsham, Pa. 19044 (1979).

It thus appears that there is still a need for a device for efficiently administering at least one type of gas such as oxygen to a human being, especially for use on a long-term basis.

SUMMARY OF THE INVENTION

It is an object of this invention to provide a nose mask for the administration of one or more types of gases such as oxygen or mixtures of gases containing oxygen to a human being which mask is capable of efficiently delivering the gas or gases while permitting the wearer to breathe, eat and converse in as substantially normal a fashion as is possible under the circumstances. The nose mask of this invention is open beneath the wearer's nose and, when compared with nose masks which completely cover the nose, does not provide resistance to exhalation through the nose or retain significant amounts of condensed water vapor on the inside surfaces of the mask.

Another object of this invention is to provide the above type of nose mask which is simple in design, economical to produce from non-toxic, disposable or easily cleanable and sterilizable materials, lightweight, and comfortable enough to enable the mask to be worn for extended periods of time.

It is a further object of this invention to provide a nose mask which can be used to efficiently adminster gases containing a variety of concentrations of oxygen gas (e.g., 30% to 100% by volume of oxygen) over a range of gas delivery flow rates (e.g., from 1 liter/min. to 6 liters/min.) in a manner which is relatively comfortable to the patient and suitable for use in long-term oxygen therapy applications.

These and other objects are accomplished by means of a nose mask which comprises, in combination, a shell, as hereinafter described in greater detail, wherein the area beneath the wearer's nose is sufficiently open to permit free breathing and a length of hollow gas delivery tube having at least one gas delivering and dispersing means contained within an inside region of the shell which region is located below the lower edge of the wearer's nose. Each gas delivering and dispersing means must contain at least one opening having a configuration and being situated on the tube such that the gas being delivered is dispersed beneath the nose and in front of the mouth of the wearer so that a cloud of gas enriched in the gas or gases being delivered is efficiently provided to the wearer.

BRIEF DESCRIPTION OF THE DRAWINGS

The above and other objects, features and advantages of the present invention will become apparent to those skilled in the art upon examination of the following description and accompanying drawings which are merely illustrative of the present invention.

In the drawings.

DETAILED DESCRIPTION OF THE INVENTION

The present invention relates to a nose mask for administering at least one type of gas to a human being, which comprises, in combination:

(I) a shell having a rear portion, a front portion, and a first opening, said shell having a shape such that:
  (a) the rear portion has edges which substantially conform to the face of a wearer,
  (b) the front portion extends over the nose of the wearer down to a point just above the upper lip of the wearer thereby enabling the wearer to breathe, eat and converse in a substantially normal fashion, and
  (c) the first opening comprises substantially the entire horizontal area situated beneath the wearer's nose extending from the front portion to the rear portion of the shell along a line parallel to said point above the upper lip of the wearer and perpendicular to the face of the wearer; and (II) a length of hollow gas delivery tube contained within an inside region of the shell which region is defined as being the area between both sides of the front portion of the shell and the area between the lower edge of the wearer's nose and said point above the wearer's upper lip, and gas delivery tube being affixed to the shell by a suitable attachment means and being adapted to receive at least one gas supply tube, any remaining end of said tube being sealed by a suitable sealing means when only one gas supply tube is employed to provide a source of gas to said delivery tube, said gas delivery tube containing at least one gas delivering and dispersing means for allowing said gas to pass through one wall of said delivery tube and for creating a cloud of gas enriched in the gas being delivered, which means is situated on the gas delivery tube such that said cloud of gas is efficiently provided directly beneath the nose and in front of the mouth of the wearer, there being at least one gas delivering and dispersing means which extends horizontally over the surface of the gas delivery tube for a distance which is greater than the internal diameter of said hollow delivery tube.

Figure 1:
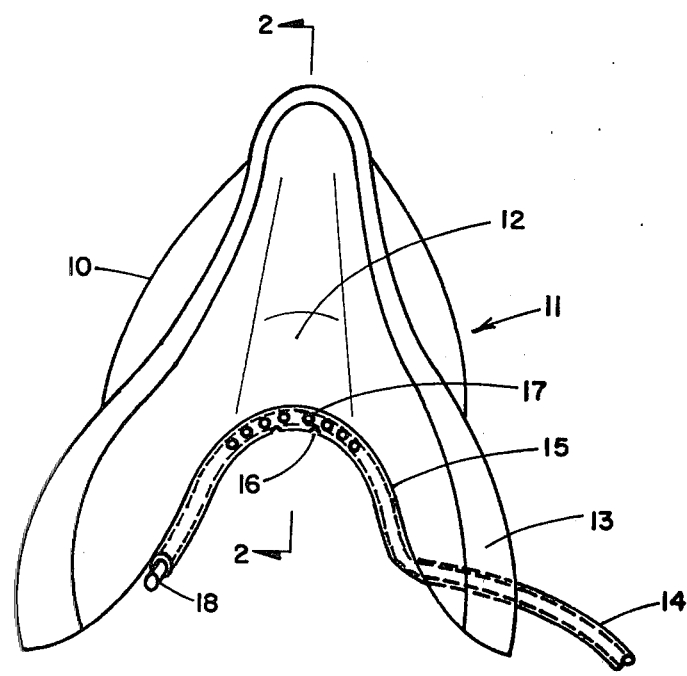
FIG. 1 is a perspective view of a nose mask of the present invention taken from the rear showing the shell, gas delivery tube and one gas supply tube.

Referring to the drawings, FIG. 1 shows one embodiment of the nose mask of the present invention shown as 11 which comprises a shell 10 having both a front portion 12 and a rear portion 13 and a hollow, gas delivery tube 15. A hollow gas supply tube 14 leads to and is received by gas delivery tube 15. The gas delivery tube 15 is attached to the bottom of the shell by a suitable attachment means and extends along the bottom of the shell within an inside region which is the area between the two sides of the front portion of the shell 12 and the area between the lower edge of the wearer's nose and a point just above the wearer's upper lip. The term "within an inside region" includes a gas delivery tube which is attached beneath the lower edge of shell 10 as long as it does not interfere with the wearer's ability to breathe, eat and converse in a substantially normal fashion. The gas delivery tube 15 shown in this embodiment contains two distinct sets of gas delivering and dispersing means represented as a row of round gas delivery openings 16 and 17 which extend completely through one wall of the gas delivery tube 15. Opening 17 is one of a set of eight gas delivery openings which are positioned such that the gas being delivered is directed towards the nose of the wearer and opening 16 is one of two gas delivery openings which are positioned such that the gas being delivered is directed towards the wearer's mouth. Each set of openings is located on the tube such that the center of each opening in a set is positioned along a straight line which is parallel to the center of the gas delivery tube 15. Likewise, each set of openings is situated such that the center of each row of openings is located on a line which corresponds to the center of the wearer's nose. When each set of gas delivery openings (gas delivering and dispersing means) is measured from end to end, at least one set extends horizontally over the surface of the hollow gas delivery tube 15 for a distance which is greater than the internal diameter of the hollow gas delivery tube 15. In FIG. 1, both sets extend horizontally over the surface of tube 15 for a distance which is greater than the internal diameter of gas delivery tube 15. To obtain best gas dispersion, it may be preferable to have the total cross-sectional area of all gas delivery openings located on the gas delivery tube be about equal to the total cross-sectional area of the hollow portion of the gas supply tube. The other end of the gas delivery tube contains a sealing means which is shown as a plug 18 inserted into the end of gas delivery tube 15. In this embodiment, the gas delivery tube 15 is shown as being an extension of the gas supply tube 14.

Figure 2:
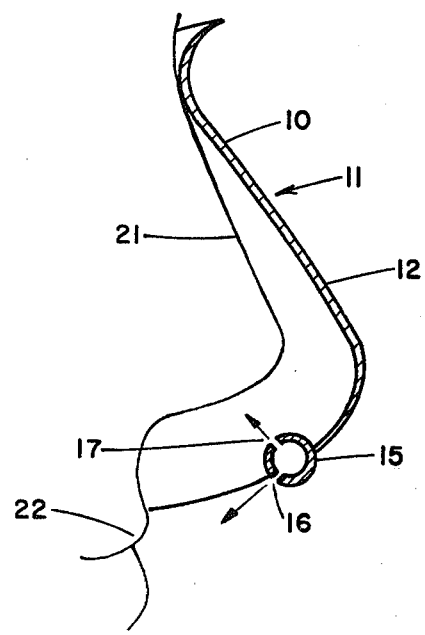
FIG. 2 is a cross-sectional view of FIG. 1 taken along section line 2'2 showing both the positioning of the gas delivery tube along the bottom of the shell and the positioning of the gas delivery openings in relation to the wearer's face.

FIG. 2 is a cross-sectional view of nose mask 11 along section line 2—2 showing the gas delivery tube 15 attached to the edge of the front portion 12 of shell 10. In this and the other cross-sectional views which follow, each set of gas delivery openings comprising the gas delivering and dispersing means is shown for the purpose of clearly showing the positioning of each set of gas delivery openings on the gas delivery tube even though some sets of openings may not have an opening which falls directly on the section line. FIG. 2 shows that gas delivery tube 15 contains two distinct gas delivering and dispersing means which are two sets of openings represented by openings 16 and 17 which sets are separated by a 90° angle and positioned such that the gas being delivered is directed (as shown by the arrows) at the nose 21 and the mouth 22 of the wearer.

The shell and gas delivery tube can be manufactured from any suitable material which is capable of being formed into and retaining the shape described above. Thus, rigid plastic, metal or flexible polymeric materials such as polystyrene, aluminum or natural rubber can be used. Preferably, the nose mask is constructed from a soft, flexible polymeric material, such as polyvinyl chloride, an ethylene/vinyl acetate copolymer, polyethylene, polypropylene, silicone rubber, natural rubber, and other thermoplastic rubbers such as a polyurethane elastomer, which is non-toxic, sterilizable, and either pigmented or unpigmented and preferably flesh-colored when non-transparent pigmented materials are used.

As shown more clearly in FIG. 2, the front portion 12 of the shell 10 is slightly curved at the bottom and extends down past the lower edge of the wearer's nose 21 to a point just above the wearer's upper lip 22, the remainder of the shell 10 being open beneath the wearer's nose to permit free breathing and to allow a cloud of gas enriched in the gas being delivered to extend over the wearer's mouth. This open area comprises substantially the entire horizontal area situated beneath the wearer's nose extending from the front portion 12 to the rear portion 13 of the shell 10 along a line parallel to said point just above the upper lip 22 of the wearer and perpendicular to the face of the wearer. The term "substantially" is intended to mean that the curved end of front portion 12 can optionally be extended a short distance back towards the face of the wearer in alternative embodiments (see extension 72A of FIG. 8A) such that substantially the entire area beneath the wearer's nostrils is left open, including the area beneath the point where the nose and upper lip of the wearer meet, provided that such extension does not interfere with free breathing or reduce the efficiency of gas delivery significantly. Preferably, the entire area, as shown in FIG. 2, is left open.

The term "rear portion" of the shell is used in a broad sense to encompass the edges of the shell which come in actual contact with the wearer's face and can be a) an upturned portion of the shell 10 shown as 13 in FIG. 1; b) a simple, but somewhat sharp and less comfortable, edge which rests directly on the face (not shown) which could be used for short-term use and can be illustrated by simply cutting off rear portion 13 in FIG. 1 while following the contours of the rear portion 13 or c) a soft, flexible piece of slitted tubing (not shown) which is placed over the latter sharp edge to render the mask more comfortable to wear. The purpose of the rear portion is to seal the mask against the wearer's face in as comfortable and complete a manner as possible and therefore the term "substantially" conform is used since faces differ slightly in configuration. Therfore, the upturned rear portion 13 of FIG. 1 is preferred because it is simple, readily comforms to the face of the wearer and is easily molded as part of the shell.

Any type of attachment means or a combination of several can be employed to secure the gas delivery tube to the shell such as adhesives, room temperature or heat vulcanizable sealants or openings in the side of the shell or loops cemented to the sides of the shell through which the tube is passed. Another means by which the gas delivery tube can be attached to the shell is to simply mold the gas delivery tube as part of the front portion of the shell in one operation.

For the purposes of the present invention, a gas delivery tube is defined to be a hollow tube or a reasonable equivalent of a hollow tube which contacts the shell and falls within said inside region. One or more hollow gas supply tubes are employed to supply gas to the gas delivery tube and the supply tube can be connected to the delivery tube by several means. One means is shown in FIG. 1 wherein the one end of the supply tube is sealed and provided with one or more gas delivering and dispersing means form a combination supply and delivery tube. Alternatively, the supply tube can pass through the shell (thereby becoming a portion of the "gas delivery tube" as the term is used in this specification and the appended claims) and be attached to a second larger or smaller diameter tube (shown in FIG. 5, infra) possessing one or more gas delivering and dispersing means by, for example, slip-fitting the tubes together. Alternatively, the gas delivery tube can be provided with an extension outside of the shell onto which the supply tube is attached.

Since a hollow tube generally has at least two openings perpendicular to its length or at least across its inner diameter (exclusive of any openings passing through only one wall), if only one gas supply tube is connected to the gas delivery tube, the other end of the tube is preferably sealed by means of a sealing means such as a plug of solid material, closed by soldering or simply heat-sealed if the tube is a thermoplastic material. It will be readily apparent to one skilled in the art that an opening can be made in the center of the gas supply tube which only passes through one wall of the tube and is sufficiently large to receive a gas supply tube. In that event, the two remaining ends of the tube are sealed as above.

One of the primary advantages of the nose mask of the present invention resides in its ability to "efficiently" provide the gas being delivered to the wearer. The term "efficiently" is intended to mean that the number, type and positioning of gas delivering and dispersing means is selected such that the gas being delivered is mixed with the air surrounding the wearer and is retained in front of the nose and mouth of the wearer in the form of what can be termed a "cloud" enriched in the gas being delivered for a sufficient amount of time to be readily available to the wearer for breathing. The gas being delivered is deflected by the shell and remains in front of the wearer's nose and mouth in a more concentrated amount than would be expected in the absence of the shell and therefore the nose mask effectively delivers more of the gas being supplied than a nasal cannula having prongs which direct the gas directly into the nostrils.

Figure 3:
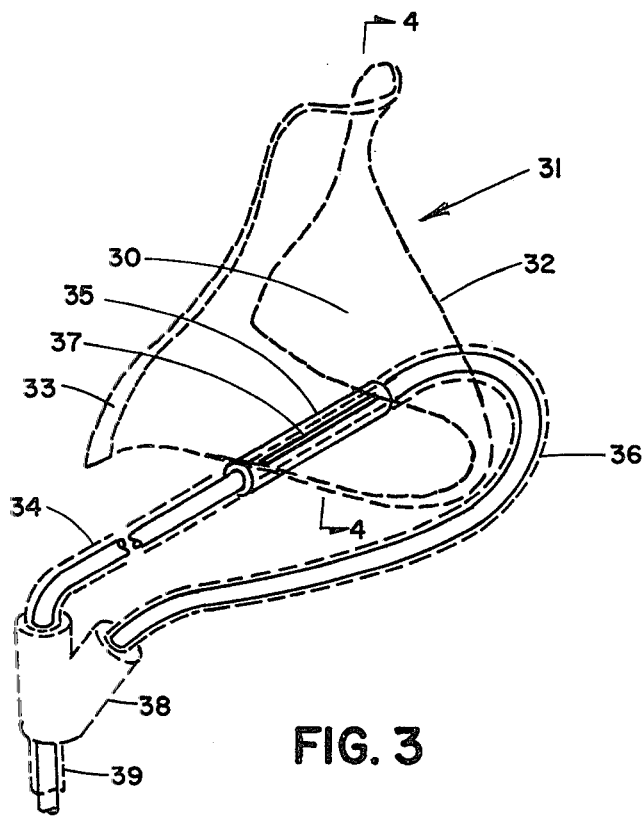
FIG. 3 is a perspective view, taken from the side, of a nose mask of the present invention containing two gas supply tubes and a single gas delivery opening.

Certain important considerations must be kept in mind in constructing a nose mask of the present invention. In its broadest sense, the gas delivery tube can contain one gas delivering and dispersing means which can simply be one opening in one wall of the gas delivery tube. Since the means must be placed on the delivery tube in such a manner that the gas being delivered is "efficiently" provided to the wearer as defined above, one large round opening in the wall of the delivery tube wall having the same diameter as that of the inner diameter of the gas delivery tube might not be sufficient to adequately provide a "cloud" of enriched gas. Therefore, at least one gas delivering and dispersing means should extend horizontally over the surface of the tube for a distance which is greater than the inner diameter of the gas delivery tube. FIG. 3 shows an embodiment of the nose mask as 31 wherein the front portion 32 and the rear portion 33 of shell 30 are shown in outline form to bring out the detail of gas delivery tube 35 which extends across the bottom of the front portion 32 and is supplied with gas on both ends of tube 35 by a first gas supply tube 34 and a second gas supply tube 36 (also shown in outline form). Tubes 34 and 36 lead to a Y-connector 38 which is fed by a common gas supply tube 39. Gas delivery tube 35 contains a gas delivering and dispersing means in the form of one gas delivery opening in the shape of a long, narrow slot 37 to provide adequate dispersion of the gas being delivered across the inside region of the shell. When the slot 37 is measured from end to end, the slot extends horizontally over the surface of the hollow gas delivery tube 35 for a distance which is greater than the internal diameter of the hollow gas delivery tube 35. As illustrated, the slot 37 extends along nearly the entire surface of tube 35 in a straight line which is parallel with the center of tube 35.

Figure 4:
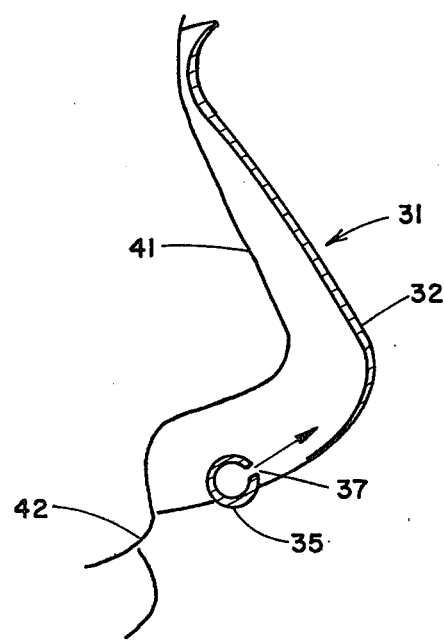
FIG. 4 is a cross-sectional view of FIG. 3 taken along section line 4—4 showing the positioning of the gas delivery tube and the opening thereon.

FIG. 4 is a cross-sectional view of the nose mask of FIG. 3 along section line 4—4 showing the relative positioning of the mask 31 relative to the wearer's nose 41 and upper lip 42. One possible positioning of the slot 37 on gas delivery tube 35 is shown in FIG. 4 wherein the gas being delivered from slot 37 is shown as an arrow which is directed at the front portion 32 of the shell between the lower edge of the front portion 32 and the wearer's nose 41.

It will be apparent from the above discussion that the gas delivering and dispersing means can take the form of many different shapes of openings passing through one wall of the gas delivery tube such as round, square, rectangular, oval, an undulating narrow slot and the like provided that the means consisting of such opening or openings functions to adequately disperse the gas being delivered to enable it to be efficiently provided to the wearer. A gas delivering and dispersing means is considered to be a set of one or more gas delivery openings which can be associated with one another such as one long, narrow slot as shown in FIG. 3 or a set of openings such as the row of eight round openings shown in FIG. 1. For example, the slot 37 of FIG. 3 need not be in a straight line, but could spiral around tube 35 if such a configuration results in better gas dispersion. To measure the distance over which a gas delivering and dispersing means extends over the surface of a gas delivery tube, one selects either the two ends of one opening or, in the case of a means which consists of a set containing a plurality of openings, the two openings which are farthest from each other and measures the farthest distance between the two openings.

In view of the need for proper dispersion and direction of the gas being supplied, it is preferred that there be at least two distinct gas delivering and dispersing means on the gas delivery tube. One means is "distinct" from another means if the line on which the set of gas delivery openings of one means are centered differs fron the line on which the set of gas delivery openings of the second means are centered. A general rule to be followed is that a large number of smaller gas delivery openings is preferable to a small number of larger openings. More preferably, the gas delivery tube contains at least two sets of gas delivering and dispersing means wherein the angle of separation between the two means which are farthest apart from each other is between 45° and 180°, preferably standard angles such as 45°, 90°, 135° or 180° are employed for ease of manufacture. Other sets of gas delivery openings can be positioned between the above two sets to provide better dispersion of the gas being supplied. It will be obvious that the gas delivering and dispersing means should not be positioned in such a way that most of the gas being delivered is directed away from both the nose and mouth of the wearer so that much of it is not available for breathing since that would be an inefficient placement of the gas delivering and dispersing means. To provide a maximum amount of gas directly to the wearer, at least one gas delivering and dispersing means can be positioned such that the gas being delivered is directed at the wearer's nose.

To provide a more comfortable nose mask for long-term wear, it can be preferable to have at least one gas delivering and dispersing means, and more preferably, all of the means, positioned such that the gas being delivered is directed at the front portion of the shell away from the wearer's nose to reduce drying of the patient's mucous membranes caused by a constant stream of gas being directed over the wearer's mucous membranes. One or more of the gas delivering and dispersing means can be positioned so that some of the gas is directed towards the mouth of the wearer. An even more preferable type of gas delivery tube would be one containing two distinct gas delivering and dispersing means separated by the above preferred angles which further contains a plurality of small gas delivery openings randomly spaced between the two gas delivering and dispersing means to provide maximum dispersion of the gas into a cloud in front of the wearer's mouth and nose which can be easily and efficiently breathed by the wearer.

The cloud of enriched gas is more comfortable to breathe than a stream of gas aimed directly into the wearer's nostrils, especially when higher flow rates such as 4 to 6 liters/minute are being supplied to the wearer as is typically the case when oxygen concentrations of from 30 percent to 50 percent by volume are used. Oxygen concentrations of about 40 percent by volume are presently available from portable, membrane-type oxygen enrichment units which are intended for home use. The nose mask of the present invention can be a useful addition to such units. Higher flow rates are generally required when lower concentrations of oxygen are being used so that the patient receives a gas mixture containing from at least 26 percent to 32 percent oxygen in the trachea of the patient's lungs since the concentration of oxygen being supplied is reduced as it is diluted with the air surrounding the wearer as he breathes. It is well known that a patient should not be given a high concentration of oxygen for a significant period of time because high concentrations of oxygen have a toxic effect on the lungs. Therefore, dilution with room air is desirable and occurs during the use of both the nasal cannula and the face mask of the present invention.

When higher flow rates are used with a nose mask wherein the gas delivery tube contains a number of smaller gas delivery openings, a single supply tube may suffice. At low (1 to 4 liters/minute) flow rates, it can be preferable to employ gas supply tubes at opposite ends of the gas delivery tube to minimize the pressure drop and consequent reduction in flow rate along a gas delivery tube containing a number of gas delivery openings.

Figure 5:
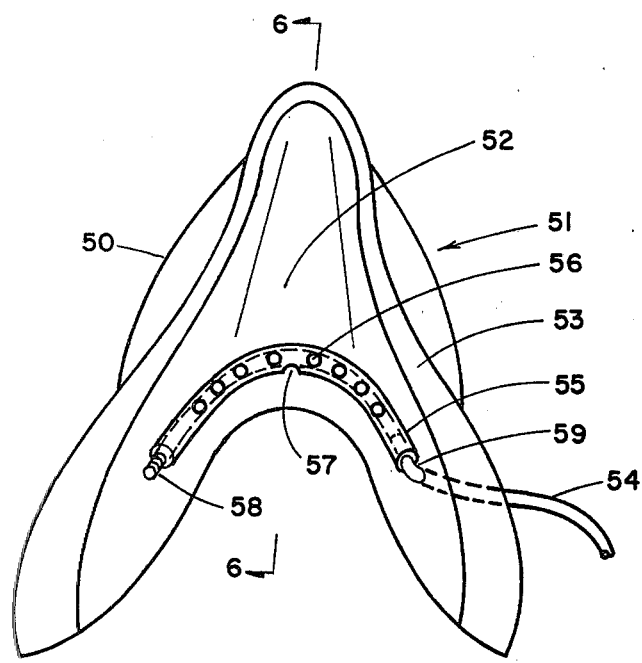
FIG. 5 is a perspective view, taken from the rear, of a nose mask of the present invention having one opening in the shell through which the gas delivery tube passes and showing the gas delivery attached to the inside of the shell.

Further embodiments of the nose mask of the present invention will now be shown and discussed. FIG. 5 shows another embodiment of the nose mask of the present invention as nose mask 51 wherein the shell 50 has a front portion 52 and a rear portion 53. A hollow gas supply tube 54 is shown leading to one side of front portion 52 and further passing through a first opening 59 to a gas delivery tube 55. Gas delivery tube 55 is attached to the inside wall of the front portion 52 and is adapted to receive gas supply tube 54 because gas delivery tube 55 has an inner diameter which is the same as the outer diameter of tube 54. Gas delivery tube 55 contains one gas delivering and dispersing means in the form of one set of eight gas delivery openings which extends across the surface of tube 55 for a distance which is greater than the internal diameter of tube 55, one of which gas delivery openings is shown as 56, another gas delivering and dispersing means which is a set containing one gas delivery opening 57 and a sealing means in the shape of a plug 58.

Figure 6:
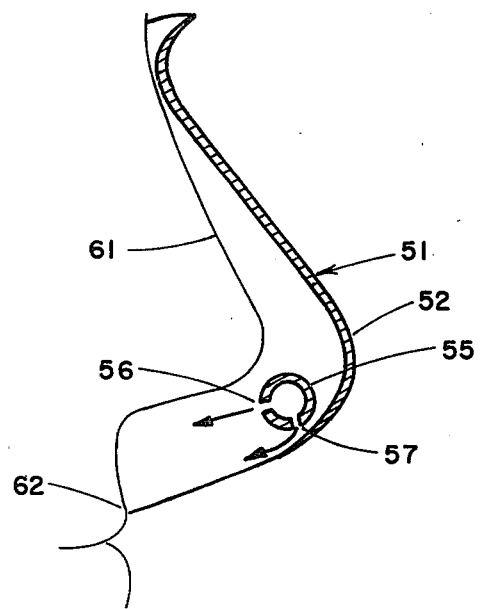
FIG. 6 is a cross-sectional view of FIG. 5 along section line 6—6 showing the positioning of the gas delivery tube and the openings thereon.

FIG. 6 shows a cross-sectional view of nose mask 51 of FIG. 5 along section line 6—6 showing how the gas delivery tube is attached along the inside wall of the front portion 52 on a plane which is even with the lower edge of the wearer's nose 61, the lower end of front portion 52 ending just above the upper lip 62 of the wearer. Gas delivery tube 55 contains two distinct gas delivering and dispersing means shown as two sets of gas delivery openings separated by a 90° angle, one set (represented by opening 56) being directed towards the face of the wearer and the other see (represented by opening 57) being directed at the lower edge of the mask such that the gas being delivered is directed as shown by the arrows. Positioning the gas delivery tube 55 below the tip of the wearer's nose along the inside of the front portion 52 of the shell 50 as shown in FIGS. 5 and 6 is preferred because it leaves the area beneath the nose 61 completely open.

Figure 7:
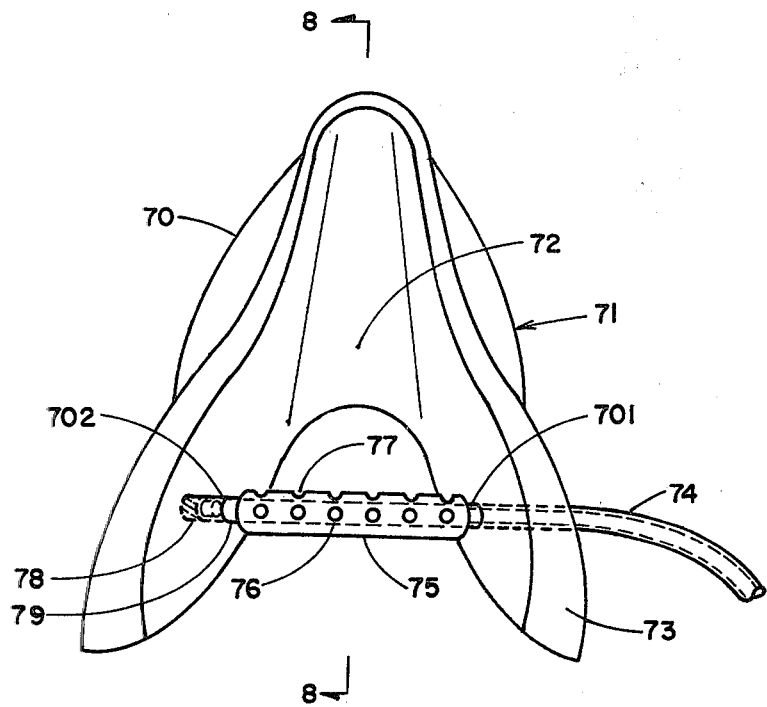
FIG. 7 is a perspective view, taken from the rear, of a nose mask of the present invention containing two openings in the shell through which the gas delivery tube passes wherein the holes are located such that the gas delivery tube passes beneath the wearer's nose.

FIG. 7 shows still another embodiment of the nose mask of the present invention as transparent nose mask 71 wherein the shell 70 has a front portion 72 and a rear portion 73. Hollow gas supply tube 74 passes through a first opening 701 into gas delivery tube 75 which gas delivery tube 75 passes beneath the nose of the wearer and is connected to extension tube 79 which passes through a second opening 702 and terminates with a sealing means which is pictured as plug 78 in extension tube 79. Gas delivery tube 75 contains two distinct gas delivering and dispersing means in the form of two rows of six gas delivery openings wherein adjacent openings are equally spaced from each other, one of each opening being shown as opening 76 and opening 77, respectively. The gas delivering and dispersing means are separated by a 90° angle.

Figure 8A:
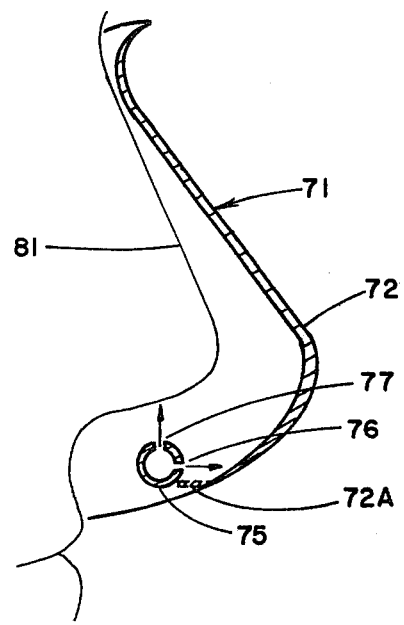
FIGS. 8A, 8B, 8C and 8D are cross-sectional views of FIG. 8 along section line 8—8 showing alternative placings of the two sets of gas delivery openings on the gas delivery tube.

FIGS. 8A, 8B, 8C and 8D are cross-sectional views of nose mask 71 of FIG. 7 taken along section line 8—8 showing various placements of the gas delivering and dispersing means on the gas delivery tube. FIG. 8A shows the nose mask 71 as it is illustrated in FIG. 7 wherein the gas delivery tube 75 is located beneath the nose 81 of the wearer and contains two gas delivering and dispersing means spaced apart by a 90° angle wherein one means (represented by opening 77) is situated such that the gas being delivered is directed at the nose of the wearer and the other means (represented by opening 76) is situated such that the gas being delivered is directed at the front portion 72 of the mask. The direction of gas flow is shown by the arrows. This embodiment is simple to manufacture and the gas delivery tube 75 passing through both sides of the mask lends support to the mask itself. Additionally, the front portion 72 can contain ribs (not shown) to further support the mask.

FIG. 8A also shows an optional extension of front portion 72 as extension 72A which extends back towards the face of the wearer, but leaves substantially the entire area beneath the wearer's nostrils open, including the area beneath the point where the nose and upper lip of the wearer meet.

Figure 8B:
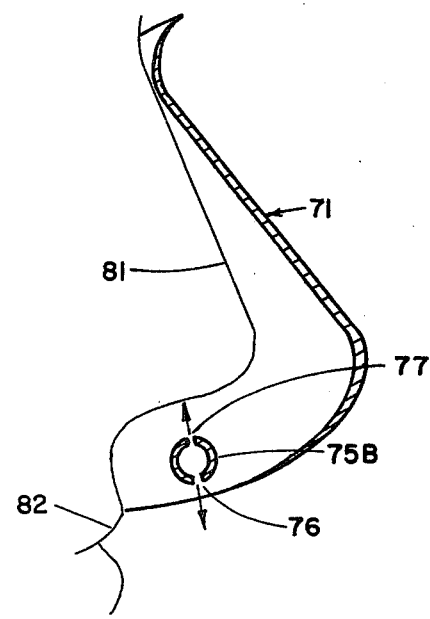

FIG. 8B shows an alternative placing of the gas delivering and dispersing means on nose mask 71 wherein the means represented by opening 77 and the means represented by opening 76 are separated by an angle of 180° on the gas delivery tube 75B such that the gas being delivered (as shown by the arrows) is directed at the nose 81 of the wearer and in the direction of the wearer's mouth 82.

Figure 8C:
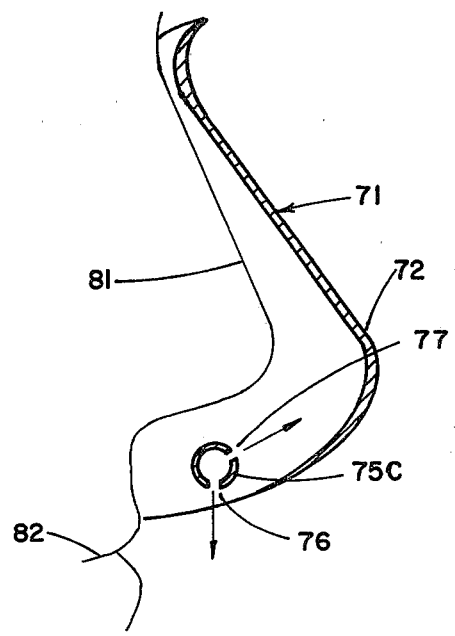

FIG. 8C shows another alternative placing of the sets of gas delivery openings on nose mask 71 wherein the gas delivering and dispersing means represented by opening 77 and the means represented by opening 76 are separated by an angle of 135° on the gas delivery tube 75C such that the gas being delivered (as shown by the arrows) is directed away from the wearer's nose 81 towards the front portion 72 of the mask and in the direction of the wearer's mouth 82.

Figure 8D:
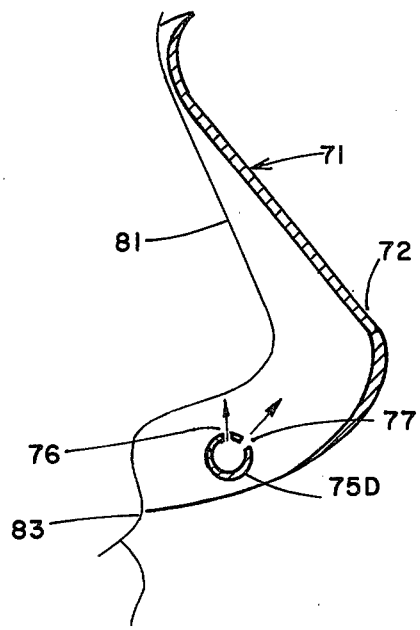

FIG. 8D shows still another alternative placing of the gas delivering and dispersing means on nose mask 71 wherein the means represented by opening 77 and the means represented by opening 76 are separated by an angle of 45° on the gas delivery tube 75D such that the gas being delivered (as shown by the arrows) is directed at the wearer's nose 81 and at the wearer's upper lip 83.

Figure 9:
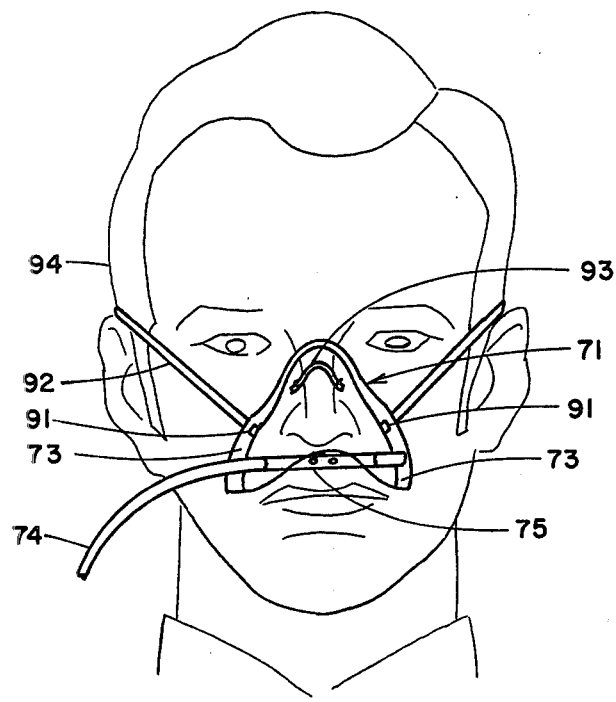
FIG. 9 shows a front view of the nose mask of FIG. 7 as it would appear on the face of a wearer.

FIG. 9 shows the transparent nose mask 71 illustrated in FIG. 7 as it would appear on the face of the wearer 94 when viewed from the front. The gas supply tube 74 and the gas delivery tube 75 are shown. The rear portion 73 of the mask contains a slit-like opening 91 on both sides through which an elastic band 92 is passed for the purpose of retaining the mask on the wearer's face. A pliable aluminum clip 93 is provided to allow the wearer 94 to adjust the fit of the mask over the nose.

Figure 10:
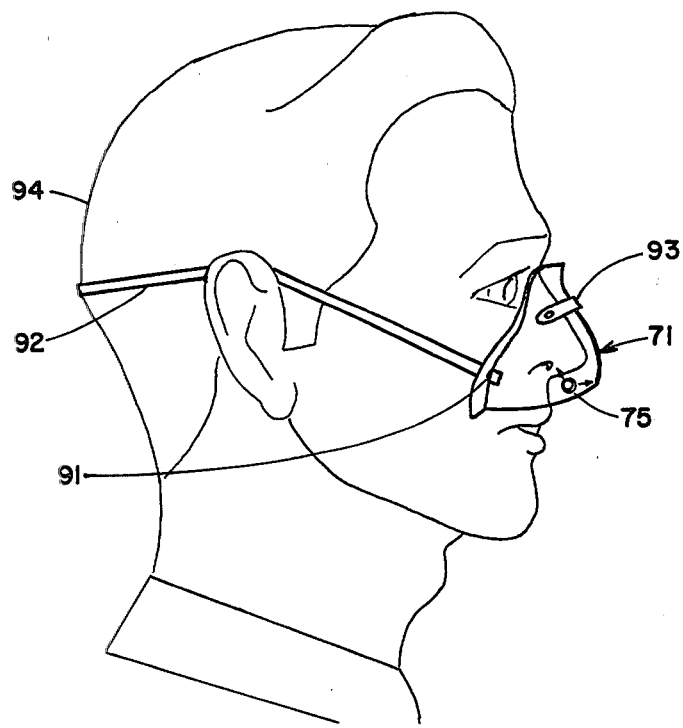
FIG. 10 shows a side view of the nose mask of FIG. 7 as it would appear on the face of a wearer, the gas supply tube being omitted for the purpose of clarity.

FIG. 10 shows a side view of nose mask 71 as shown in FIG. 9 on wearer 94 showing the gas delivery tube 75 with arrows to show the direction of the gas being delivered. The gas delivery tube 74 shown in FIG. 9 is omitted while opening 91, band 92 and clip 93 are the same as in FIG. 9.

Figure 11:
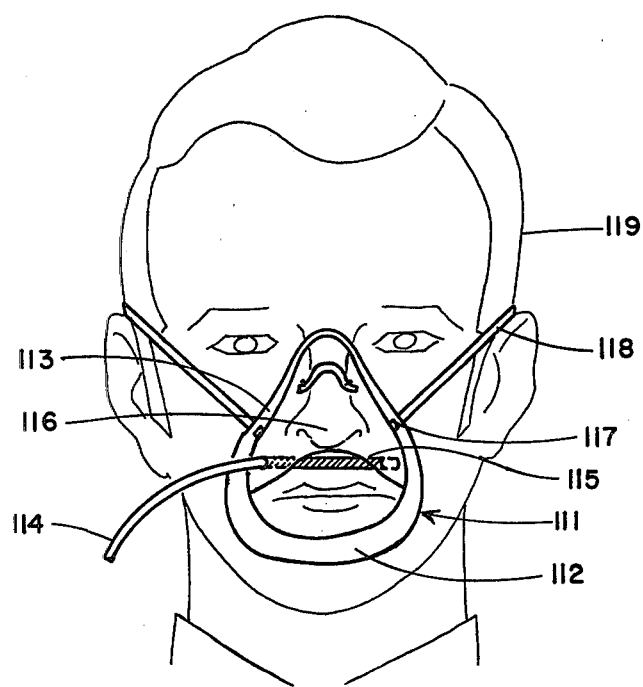
FIG. 11 shows a front view of an alternative embodiment of the nose mask of the present invention as it would appear on the face of a wearer which mask further contains an extension of the rear portion of the shell extending around, but not covering, the mouth of the wearer.

FIG. 11 shows an alternative embodiment of the nose mask of the present invention as nose mask 111 containing a rear portion 113 which further contains an extension 112 of the rear portion 113 which substantially conforms to the face of the wearer and encircles, but does not cover, the mouth of the wearer 119. Nose mask 111 is otherwise the same as the other previously-described embodiments (see FIG. 7) and has a front portion 116 containing a gas delivery tube 115 connected with a gas supply tube 114. As in FIG. 9, the nose mask 111 is shown with a slit-like opening 117 on both sides of the rear portion 113 through which is passed an elastic band 118 to hold the mask on the face of the wearer.

Several prototype masks of the present invention were constructed for the purpose of comparing the efficiency of oxygen delivery of a nose mask of the present invention with that of a nasal cannula. The details of constructing a nose mask of the present invention will be readily apparent to one skilled in the art from the foregoing discussion and drawings, but to further aid others in the practice of the present invention, the construction of the prototype masks illustrated in FIG. 7 will be described.

Several disposable oxygen masks fitted with rebreather bags of the type shown in U.S. Pat. No. 2,843,121 (Hudson—patented July 15, 1958) were commercially obtained. The shell portion, which was manufactured from a flexible, transparent polyvinyl chloride material, was cut along its bottom edge such that the entire bottom portion of the mask below a line corresponding to the upper lip of a wearer was open to the atmosphere. Since the mask obtained was a rebreather type, the shell contained exhalation openings on both sides of the shell and those holes were sealed with a round patch to result in a solid shell having a front portion 72 and a rear portion 73 (see FIG. 7). A first circular opening 701 and a second circular opening 702 having a diameter of slightly less than 6 millimeters (mm) in diameter were placed about two centimeters (cm) from the rear portion of the mask. A length of hollow, flexible polyvinyl chloride gas supply tube 74 having an outside diameter (O.D.) of 6 mm and an inside diameter (I.D.) of 4 mm was obtained and about 8 mm of one end of the supply tube was passed through opening 701 which opening was large enough to allow the tubing to be pulled through, but small enough to snugly hold the tube in place. A gas delivery tube 75 was constructed from a 5 cm length of hollow, flexible polyvinyl chloride tubing having an 8 mm O.D. and a 6 mm I.D. To provide two distinct sets of gas delivering and dispersing means, two rows of six round one-sixteenth inch (1.59 mm) diameter gas delivery openings were placed 90° apart from each other on the gas delivery tube 75 shown in FIG. 7 wherein the spacing between any two adjacent openings in the same set was one-eighth inch (3.18 mm) from center to center. One end of the delivery tube 75 was slipped over the portion of the supply tube passing through opening 701. The other end of tube 75 was partially slipped over the end of a 2 cm length of 6 mm O.D., 4 mm I.D., polyvinyl chloride extension tube 79 and the remainder of the tube 79 was passed through opening 702 and a solid polyvinyl chloride plug 78 was inserted into the opening to complete the assembly. The gas delivery tube was then turned to correspond to the configuration shown in FIG. 7 and 8A such that the gas being delivered was directed at the wearer's nose and at the front portion 72 of the nose mask. The center of each row of gas delivery openings was located beneath the approximate center of the wearer's nose. The completed nose mask also contained an elastic band 92 passing through holes 91 on both sides of the mask to hold the nose mask on the wearer's face and a clip 93 to adjust the fit of the mask as shown in FIG. 9. In this mask, the calculated total cross-sectional area of twelve round 1.59 mm diameter gas delivery openings (23.8 square millimeters) is greater than the total cross-sectional area of the 4 mm I.D. gas supply tube (12.6 square millimeters).

Another mask was constructed in the same manner, but instead of having two rows of six gas delivery openings separated by an angle of 90°, the gas delivery tube contained two rows of gas delivery openings separated by an angle of 180°. The latter mask contained one row of eight round one-sixteenth inch (1.59 mm) diameter openings wherein the spacing between any two adjacent openings was about one-eighth inch (3.18 mm) from center to center and a second row of two round one-sixteenth inch (1.59 mm) diameter openings wherein the spacing between the centers of the openings was three-eighths inch (9.52 mm). As above, both sets were centered such that the center of each row was located beneath the approximate center of the wearer's nose, the row of eight openings being positioned such that the gas being delivered was directed at the wearer's nose and the other row being positioned such that the gas being delivered was directed in the direction of the wearer's mouth.

EXAMPLES

The prototype nose mask described above (two rows of six gas delivery openings separated by a 90° angle) was compared to a nasal cannula of the type described in U.S. Pat. No. 2,868,199 which cannula contained two nasal prongs for delivering a stream of gas directly into each nostril of the wearer. The nasal cannula was used because it is a simple nasal oxygen delivery device which is frequently used for oxygen therapy because it permits the patient to breathe, eat, converse and move about with a minimum of restrictions. The efficiency of oxygen delivery of each type of mask was compared by measuring the percent oxygen saturation of blood in the ear of the person wearing the mask. Two concentrations of gases were employed: 100 percent by volume oxygen and 30 percent by volume oxygen wherein the remainder of the gases in the latter were primarily nitrogen and trace amounts of other inert gases.

The instrument employed to continuously measure the oxygen saturation of the wearer's blood was a Hewlett-Packard Model 47201A Ear Oximeter obtained from the Hewlett-Packard Company, Waltham Division, Waltham, Mass. 02154. The instrument had an earprobe which was first internally calibrated. Then, the sensing portion (a gap in one end) of the earprobe was slipped over the anti-helix (pinna) of the wearer's ear (the flat part just within the curl of the ear's outer edge) after this part of the ear had been rubbed briskly for about 15 seconds to stimulate the flow of arterial blood. Once in place, the instrument gives a direct reading in percent oxyhemoglobin. According to the manufacturer, this reading corresponds to arterial blood oxygen saturation if ear perfusion is far in excess of metabolic demands as is usually the case in that part of the ear. The instrument thus provides a non-invasive (no blood samples are withdrawn) method for continuously determining and monitoring the oxygen saturation in arterialized capillary blood in a manner which is both accurate and comfortable to the patient. See Scoggin et al., "Clinical Evaluation of a New Ear Oximeter," Heart and Lung: The Journal of Critical Care, 6, pp. 121-126 (1977) and Merrick et al., "Continuous, Non-Invasive Measurements of Arterial Blood Oxygen Levels," Hewlett-Packard Journal, Hewlett-Packard Company, Palo Alto, Calif. 94304, Vol. 28(2), pp. 2-9 (1976) which are both hereby incorporated by reference to teach the use of the instrument and the significance of the readings obtained. All arterial blood oxygen saturation levels hereinafter reported were obtained using the above Ear Oximeter.

Since a normal, healthy person will generally have an arterial blood oxygen saturation level of between 95 to 98%, differences in saturation levels due to the effect of added oxygen will be rather small since the blood of such a person is almost completely saturated with oxygen. For this reason, two COPD patient volunteers were chosen and the following comparison studies were conducted in a hospital under the close supervision of two physicians.

Patent A was a female patient afflicted with bronchitis. The patient was fitted with the above nasal cannula for the purposes of comparison. The gas supply tube leading to the nasal cannula was connected to a source of 100 percent by volume oxygen (hereinafter 100 percent oxygen) and the gas was directed to the patient at a flow rate of 2 liters/minute which is a reasonable flow rate for supplying this concentration of oxygen. After a short time, the reading on the Ear Oximeter became reasonably steady at 94% arterial blood oxygen concentration (oxyhemoglobin concentration). The flow rate was then increased to 4 liters/minute and a reading of 96% was obtained. The same patient was then fitted with the above-described nose mask of the present invention and after the reading became reasonably steady, a reading of 98.5% arterial blood oxygen concentration was obtained employing 100 percent oxygen at a flow rate of 2 liters/minute. Thus, the nose mask of the present invention appeared to be capable of more efficiently delivering the oxygen gas being supplied to this patient than the nasal cannula, even when a higher gas flow rate was employed with the nasal cannula. It is obvious that higher flow rates tend to waste expensive gas if the gas is not being efficiently delivered to the patient.

Patient A was again fitted with a nasal cannula and a mixture of oxygen and inert gases containing 30 percent by volume oxygen (hereinafter 30 percent oxygen) was supplied to the patient at a flow rate of 4 liters/minute. Due to her condition, she became uncomfortable and was unable to tolerate this lower concentration of oxygen (arterial blood oxygen saturation level was 88% and falling) and the testing was discontinued.

Patient B was a younger male COPD patient afflicted with cystic fibrosis. This patient had an arterial blood oxygen saturation reading of 92% when breathing room air. He was then fitted with the above nasal cannula which was connected to a source of 100 percent oxygen. Table I shows the arterial blood oxygen saturation readings ($O_2$ Saturation) at the indicated flow rates and oxygen concentration ($O_2$ Conc.). The nasal cannula was then connected to a gas source containing 30 percent oxygen and the readings obtained at various flow rates are shown in Table I for comparative purposes. Then, the patient was fitted with the above nose mask of the present invention and 30 percent oxygen was supplied to the patient at various flow rates. The results are shown in Table I. At 2 and 4 liter/minute flow rates, the mask of the present invention appears to be more efficient than the nasal cannula while at a 6 liters/minute flow rate, the cannula is slightly better. It should be noted that the nose mask of the present invention resulted in a 95% reading at a flow rate of 4 liters/minute while the nasal cannula required a flow rate of 6 liters/minute to produce a 95% reading.

A nose mask of the above type (FIG. 7) was constructed and a piece of polyvinyl chloride sheeting was glued onto the mask so that a portion of the area directly beneath the front portion of the wearer's nose was covered while most of the area immediately beneath the nostrils was open (see FIG. 8A, extension 72A). This mask was then placed on Patient B and employing a source of 30 percent oxygen at a flow rate of 4 liters/minute, the arterial blood oxygen saturation reading obtained was 93% which was slightly better than the nasal cannula at that oxygen concentration and flow rate.

TABLE I

| $O_2$ Conc.[a] | Flow Rate[b] | $O_2$ Saturation | |
|---|---|---|---|
| | | Nasal Cannula | Nose Mask |
| 100% | 2 | 95 | (c) |
| 100% | 4 | 96 | (c) |
| 100% | 6 | 97 | (c) |
| 30% | 2 | 92 | 94 |
| 30% | 4 | 92 | 95 |
| 30% | 6 | 95 | 94 |

[a] Oxygen Concentration from supply source, percent by volume.
[b] liters/minute
[c] Not Evaluated The nose masks evaluated above demonstrate that the nose masks are capable of delivering oxygen and mixtures of gases containing oxygen at least as efficiently as the nasal cannula and in most cases, more efficiently while being comfortable to the wearer and allowing him to breathe, eat and converse in a substantially normal fashion. Due to the improvement in efficiency, it may be possible to reduce the flow rate of the oxygen mixture while still retaining a sufficient blood oxygen saturation level in the patient to render him comfortable and thus reduce the cost of supplying oxygen to such a patient. As discussed above, it will become apparent to those skilled in the art that other types of gas delivering and dispersing means may be employed and positioned such that further improvements in efficiency of delivery can be obtained. Optimization of efficiency is further aided through the use of the above described Ear Oximeter which does not require that actual blood samples be taken from the person being tested. Thus, the above samples were provided for the purpose of illustration and are not to be construed as limiting the scope of the present invention, which is properly defined by the appended claims.

Furthermore, other modifications and variations of the nose mask of the present invention will become apparent to those skilled in the art from an examination of the above specification and drawings. Other gases, such as anesthetic gases, in addition to oxygen and other inert gases might possibly be supplied with the nose mask of the present invention and the use of such gases may necessitate a specific type of gas delivering and dispersing means. Thus, other variations of the nose mask of the present invention may be made which fall within the scope of the appended claims even though such variations were not specifically discussed above.

That which is claimed is:

1. A nose mask for providing oxygen therapy to a human being which consists essentially of, in combination:
   (I) a shell having a rear portion, a front portion, and a first opening, said shell having a shape such that:
      (a) the rear portion has edges which substantially conform to and thereby seal the shell against the face of the wearer along the entire length of the rear portion and below the eyes of a wearer,
      (b) the front portion is adapted to extend over the nose of the wearer from the bridge of the nose down to a point just above the upper lip of the wearer such that no portion of said front portion normally extends below the upper lip of the wearer, thereby enabling the wearer to breathe, eat and converse in a substantially normal fashion, and
      (c) the first opening comprises substantially the entire horizontal area situated beneath the wearer's nose extending from the front portion to the rear portion of the shell along a line parallel to said point above the upper lip of the wearer and perpendicular to the face of the wearer;
      (d) wherein said shell additionally includes an extension of the rear portion of said shell which substantially conforms to and is adapted to rest upon the face of the wearer and encircles, but does not cover, the mouth of the wearer such that the area perpendicular to and extending away from the mouth of the wearer is completely open and provides no hindrance to eating; and
   (II) a length of hollow gas delivery tube contained within an inside region of the shell which region is defined as being the area between both sides of the front portion of the shell and the area between the lower edge of the wearer's nose and said point above the wearer's upper lip, the gas delivery tube being affixed to the shell by a suitable attachment means and being adapted to receive at least one gas supply tube, any remaining end of said tube being sealed by a suitable sealing means when only one gas supply tube is employed to provide a source of pure oxygen gas or a mixture of gases containing greater than 30 percent by volume of oxygen gas to said delivery tube, said gas delivery tube containing at least one gas delivering and dispersing means for allowing said gas or mixture of gases to pass through one wall of said delivery tube and for creating a cloud of gas enriched in the gas or mixture of gases being delivered, which means is situated on the gas delivery tube such that said cloud of gas is efficiently provided directly beneath the nose and in front of the mouth of the wearer, there being at least one gas delivering and dispersing means which extends longitudinally over the surface of the gas delivery tube for a distance which is greater than the internal diameter of said hollow delivery tube.

2. The nose mask as claimed in claim 1 wherein said gas delivery tube is provided with at least two distinct gas delivery and dispersing means and the first opening consists of the entire horizontal area beneath the wearer's nose extending from the front portion to the rear portion of the shell along a line parallel to said point above the wearer's lip and perpendicular to the face of the wearer.

3. The nose mask as claimed in claim 2 wherein at least one portion of said attachment means is a second opening which extends through the shell at a point below a horizontal plane defined by the lower edge of the wearer's nose, one end of said gas delivery tube passing through said second opening.

4. The nose mask as claimed in claim 3 wherein a further portion of said attachment means is a third opening in the shell through which the opposite end of said gas delivery tube is passed, said third opening being located in the same general location on the shell as is the second opening, but is located on the side of the shell opposite to that of the second opening.

5. The mask as claimed in claims 2, 3 or 4 wherein said gas delivery tube is fitted with a flexible gas supply tube at one end and is sealed with a suitable sealing means on the opposite end.

6. The mask as claimed in claims 2 or 4 wherein said gas delivery tube is fitted with two hollow flexible gas supply tubes, one at each end of said gas delivery tube.

7. The nose mask as claimed in claims 2 or 4 wherein the gas delivery tube extends from one side of the shell to the other side in a straight line beneath the nose of the wearer.

8. The nose mask as claimed in claim 2 wherein the gas delivery tube extends along the inside of the shell along a line situated between the lower edge of the wearer's nose and said point above the wearer's upper lip.

9. The nose mask as claimed in claim 2 wherein the two distinct gas delivering and dispersing means which are farthest apart from each other are separated by an angle of between 45° and 180°.

10. The nose mask as claimed in claim 9 wherein at least one gas delivering and dispersing means is positioned such that the gas being delivered is directed at the wearer's nose.

11. The nose mask as claimed in claim 9 wherein at least one gas delivering and dispersing means is positioned such that the gas being delivered is directed at the front portion of the shell away from the wearer's nose.

12. The nose mask as claimed in claim 1 wherein said gas delivering and dispersing means is a narrow slit extending across a portion of the surface of said gas delivery tube.

13. The nose mask as claimed in claims 1 or 2 wherein each gas delivering and dispersing means consists of a plurality of round gas delivery openings.

14. The nose mask as claimed in claims 1 or 2 wherein the nose mask is provided with a length of hollow gas supply tube and said gas delivery tube is an extension of the gas supply tube.

15. A nose mask for administering at least one type of gas to a human being, which comprises, in combination:
   (I) a shell having a rear portion, a front portion, and a first opening, said shell having a shape such that:
      (a) the rear portion has edges which substantially conform to the face of a wearer,
      (b) the front portion is adapted to extend over the nose of the wearer from the bridge of the nose down to a point just above the upper lip of the wearer thereby enabling the wearer to breathe, eat and converse in a substantially normal fashion, and
      (c) the first opening consists of the entire horizontal area situated beneath the wearer's nose extending from the front portion to the rear portion of the shell along a line parallel to said point above the upper lip of the wearer and perpendicular to the face of the wearer; and
   (II) a length of hollow gas delivery tube contained within an inside region of the shell which region is defined as being the area between both sides of the front portion of the shell and the area between the lower edge of the wearer's nose and said point above the wearer's upper lip, the gas delivery tube extending from one side of the shell to the other in a straight line beneath the nose of the wearer, being affixed to the shell by a suitable attachment means and being adapted to receive at least one gas supply tube, any remaining end of said tube being sealed by a suitable sealing means when only one gas supply tube is employed to provide a source of gas to said delivery tube, said gas delivery tube containing two distinct gas delivering and dispersing means which are two rows of six round gas delivery openings separated by a 90° angle wherein the openings pass through one wall of said gas delivery tube and wherein adjacent openings are equally spaced from each other across the length of said tube and are situated such that the center of each row is located on a line which corresponds to the center of the wearer's nose, one row being positioned such that the gas being delivered is directed up to the wearer's nose and the other row being positioned such that the gas being delivered is directed at the front portion of the shell, at least one of said rows extending longitudinally over the surface of the gas delivery tube for a distance which is greater than the internal diameter of said hollow delivery tube.

16. A nose mask for administering at least one type of gas to a human being, which comprises, in combination:
   (I) a shell having a rear portion, a front portion, and a first opening, said shell having a shape such that:
      (a) the rear portion has edges which substantially conform to the face of a wearer,
      (b) the front portion is adapted to extend over the nose of the wearer from the bridge of the nose down to a point just above the upper lip of the wearer thereby enabling the wearer to breathe, eat and converse in a substantially normal fashion, and
      (c) the first opening consists of the entire horizontal area situated beneath the wearer's nose extending from the front portion to the rear portion of the shell along a line parallel to said point above the upper lip of the wearer and perpendicular to the face of the wearer; and
   (II) a length of hollow gas delivery tube contained within an inside region of the shell which region is defined as being the area between both sides of the front portion of the shell and the area between the lower edge of the wearer's nose and said point above the wearer's upper lip, the gas delivery tube extending from one side of the shell to the other in a straight line beneath the nose of the wearer, being affixed to the shell by a suitable attachment means and being adapted to receive at least one gas supply tube, any remaining end of said tube being sealed by a suitable sealing means when only one gas supply tube is employed to provide a source of gas to said delivery tube, said gas delivery tube containing two distinct gas delivering and dispersing means separated by a 180° angle, a first gas delivering and dispersing means consisting of a row of eight round gas delivery openings wherein adjacent openings are equally spaced from each other across the length of the gas delivery tube and a second gas delivering and dispersing means consisting of a row of two round gas delivery openings wherein each of said rows is situated such that the center of each row is located on a line which corresponds to the center of the wearer's nose, one row being situated such that the gas being delivered is directed at the wearer's nose and the other means being positioned such that the gas being delivered is directed in the direction of the wearer's mouth and wherein each of said openings passes through one wall of said gas delivery tube and at least one of said rows extends longitudinally over the surface of the gas delivery tube for a distance which is greater than the internal diameter of said hollow delivery tube.

17. The nose mask as claimed in claims 15, or 16 wherein at least one of said attachment means is a second opening which extends through the shell at a point below a horizontal plane defined by the lower edge of the wearer's nose and a further portion of said attachment means is a third opening in the shell which is located in the same general location on the shell as is the second opening, but is located on the side of the shell opposite that of the second opening, one end of said gas delivery tube passing through said second opening and the opposite end of said gas delivery tube passing through said third opening.

* * * * *

UNITED STATES PATENT AND TRADEMARK OFFICE
CERTIFICATE OF CORRECTION

PATENT NO. : U.S. 4,354,488
DATED : October 19, 1982
INVENTOR(S) : DONALD M. BARTOS It is certified that error appears in the above—identified patent and that said Letters Patent is hereby corrected as shown below:

In column 4, line 13, the "2'2" should read --2-2--.

In column 10, line 50, the word "see" should read --set--.

In column 15, line 55, the word "samples" should read --examples--.

Signed and Sealed this

Nineteenth Day of July 1983

[SEAL]

Attest:

Attesting Officer

GERALD J. MOSSINGHOFF

Commissioner of Patents and Trademarks